(12) United States Patent
Jacobsen et al.

(10) Patent No.: US 6,530,934 B1
(45) Date of Patent: Mar. 11, 2003

(54) EMBOLIC DEVICE COMPOSED OF A LINEAR SEQUENCE OF MINIATURE BEADS

(75) Inventors: Stephen C. Jacobsen, Salt Lake City, UT (US); Clark Davis, Salt Lake City, UT (US)

(73) Assignee: Sarcos LC, Salt Lake City, UT (US)

( * ) Notice: Subject to any disclaimer, the term of this patent is extended or adjusted under 35 U.S.C. 154(b) by 0 days.

(21) Appl. No.: 09/588,251

(22) Filed: Jun. 6, 2000

(51) Int. Cl.$^7$ ................................................ A61B 17/08
(52) U.S. Cl. ...................................................... 606/157
(58) Field of Search ................................ 606/200, 113, 606/114, 127, 128, 151, 157

(56) References Cited

U.S. PATENT DOCUMENTS 6,015,424 A * 1/2000 Rosenbluth et al. ........ 606/200
6,033,423 A * 3/2000 Ken et al. ................... 606/200

* cited by examiner

Primary Examiner—Kevin T. Truong
(74) Attorney, Agent, or Firm—Thorpe North & Western, LLP

(57) ABSTRACT

An embolic device comprised of a linear sequence of flexibly interconnected miniature beads. The device generally comprises a flexible elongate filament having a linear sequence of miniature beads disposed thereon. The beads may be fixedly or slidably connected to the filament. The device is configured to allow the beads to compress together for pushing through a catheter to a target location and extended beyond a distal end of the catheter, whereupon the flexible string of beads may fold back upon itself so as to occupy a volume of space at the target location. The string of beads may be preconfigured to the exact length needed, or the distal end of the string may be cut or severed after placement at the target location. The beads may be porous or hollow to allow them to function as drug delivery devices, and the string of beads may have an anchor device at one end to aid in anchorage of the string within the anatomy.

39 Claims, 3 Drawing Sheets

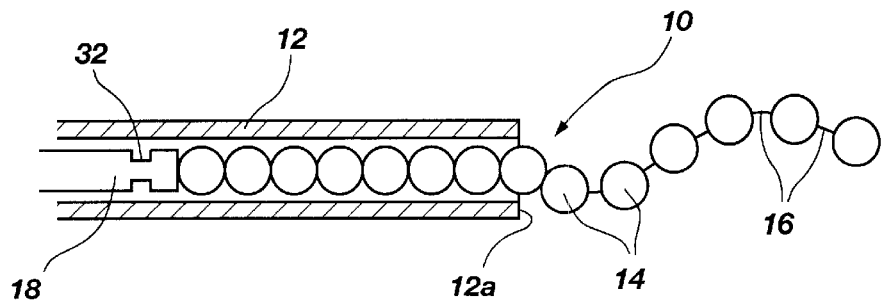
Fig. 1
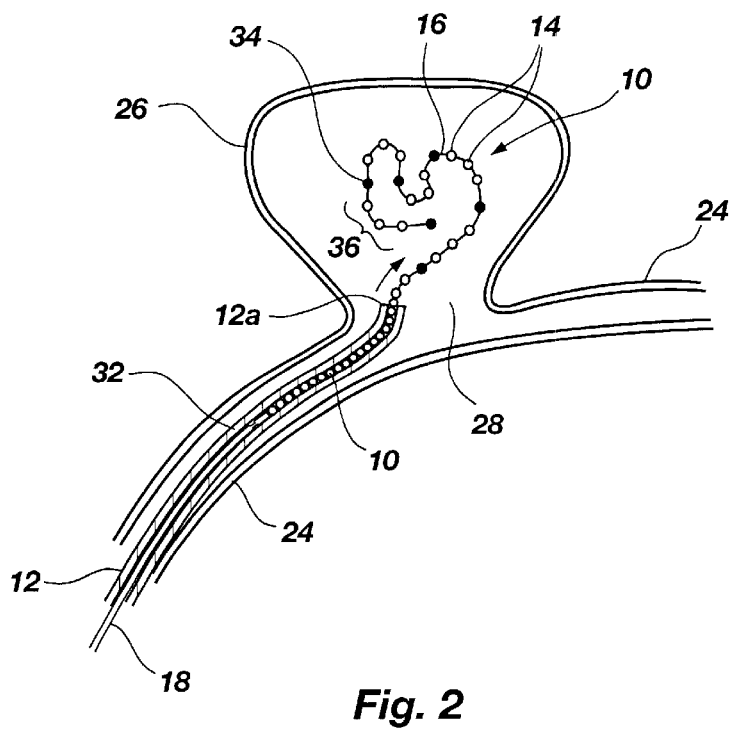
Fig. 2
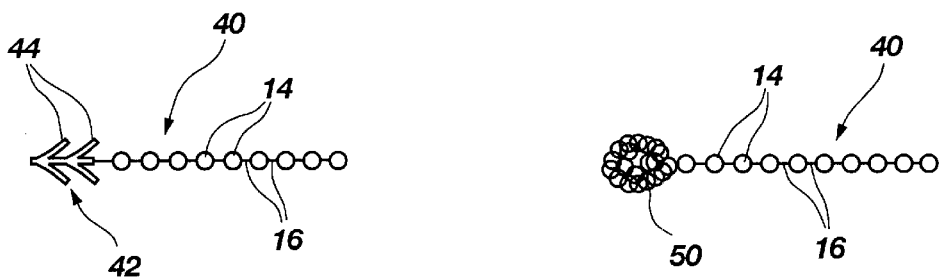
Fig. 3A  Fig. 3B

EMBOLIC DEVICE COMPOSED OF A LINEAR SEQUENCE OF MINIATURE BEADS

BACKGROUND OF THE INVENTION

1. Field of the Invention

This invention relates to endovascular devices for occluding and/or stabilizing and sealing off vasculature or body passageways, tissue defects, and aneurysms. More particularly, the present invention relates to a catheter deliverable embolic device composed of a flexibly interconnected linear sequence of miniature beads.

2. State of the Art

Devices which occlude blood flow and/or initiate blood clotting, and which can be introduced into the body via a catheter are valuable for stopping bleeding or the threat of bleeding, cutting off blood supply to a diseased organ, reducing blood flow to an organ, occluding an arterial venous malformation (avm), rebuilding a defective organ, occluding an aneurysm, etc. Devices typically utilized for these purposes include coils or particles which are deployed through a catheter to a target site where arresting blood flow is desired. In addition, various solutions, such as injectable glue, may be delivered through the catheter either for assisting and accelerating clotting or in treating the medical problem.

Typical devices used in the past include platinum coils which were inserted into the catheters and then pushed therethrough to the target site using a conventional catheter guide wire as a "plunger." The use of detachable coils appears to be gaining widest acceptance for aneurysm therapy, perhaps because of the ease and precision of control of the delivery and disposition of the coil at the desired occlusion site. The most common coil devices typically comprise 0.010" to 0.018" diameter helical coils of platinum wire, a length of the coil being twisted into larger compound coils of 1–2 cm diameter for packing into an aneurysm. One approach for delivering such coils to an occlusion site involves forming or attaching the coil at the distal end of a delivery device such as a guidewire, and then threading the coil and wire through a catheter until the coil is disposed at the occlusion site, such as the neck or opening of the aneurysm. There the coils are extended from the distal end of the catheter and placed or packed into the aneurysm cavity so as to form a mass which causes thrombogenesis and fibrogenesis, safely sealing the aneurysm to prevent rupture. The coils are then detached from the distal end of the delivery device, and the catheter is removed from the patient. Sometimes the thrombogenic coils are also provided with fibers or filaments which enhance their thrombogenecity.

Types of particles used in the past for occluding blood flow include hydrophilic particles that swell to a larger size when blood is absorbed. This swelling, of course, aids in stopping the flow of blood, assuming the positions of the particles are maintained.

However, known thrombogenic devices present some drawbacks. For example, it can be difficult to make thrombogenic coils stay in place. Because the coils are frequently made of metals with spring characteristics, the coils may tend to resist packing, and unwind out of the aneurysm. Then, like other implanted devices, the coils can migrate within the body, potentially causing trauma to body tissues or dangerous unwanted thrombosis. Likewise, hydrophilic particles also tend to become dislodged from the target site and migrate within the body.

Embolic devices, including coils, are also currently used in conjunction with cardiac revascularization procedures. In these procedures, one or more holes are made in the heart muscle itself by means of a needle, laser, or other cutting means. These holes may or may not extend completely through the heart wall so as to communicate with an interior chamber of the heart. Creating these holes initiates angiogenesis, which begins the formation of collateral blood vessels and capillaries which restore blood flow around damaged or blocked arteries to regions suffering from ischemia or inadequate blood flow. It is hypothesized that the holes promote angiogenesis through the natural release of angiogenic growth factors. Delivery into these holes using growth factors such as vascular endothelial growth factors (VEGF) may speed this process.

SUMMARY OF THE INVENTION

It would thus be desirable to have an embolic device which may be more easily packed into an aneurysm, and is less susceptible to migration within the body. It would also be desirable to have an embolic device which is unlikely to cause damage to body tissues with which it comes in contact.

It would further be desirable to have a device which can be firmly anchored into a hole formed in body tissue, and also provide means for delivering drugs which promote revascularization in the region of the hole.

It would also be desirable to have a thrombogenic or drug delivery device which dissolves within the body so as to prevent objects which could come loose and migrate through the body, potentially causing trauma or unwanted thrombogenesis.

The present invention addresses some of the above stated needs by providing a device comprising a linear sequence of flexibly interconnected miniature beads. The device generally comprises a flexible elongate filament having a linear sequence of miniature beads fixedly or slidably disposed thereon. The device is configured to allow the beads to compress together for pushing through a catheter to a target location, where the string of beads is extended beyond the distal end of the catheter, and the flexible string of beads may fold back upon itself so as to occupy a volume of space at the target location and initiate thrombogenisis there. In various embodiments, the string of beads may be configured as a drug delivery device, wherein the beads are porous or hollow, and contain a medicament for controlled release into the interior of the body. In yet another embodiment, the invention comprises a linear sequence of flexibly interconnected miniature beads having an anchor element on one end of the string for preventing migration of the string of beads.

The invention thus provides a new and improved embolic, vaso-occlusive, and drug delivery device which may be easily deployed to a target site in the human body and which is effective in inducing clotting or otherwise arresting blood flow. It also provides an embolic device which is less susceptible to expanding out of an aneurysm after being packed therein. The embolic device of the present invention is also less susceptible to migration within the body, and is less likely to cause damage or trauma to body tissues with which it comes in contact. The device may also be more firmly anchored to the site at which it is desired, and is more capable of packing a body cavity to completely thrombose it. The device may also deliver medicament to the site at which it is deployed within the body, whether functioning as an embolic device or not.

Other advantages and features of the present invention will be apparent to those skilled in the art, based on the following description, taken in combination with the accompanying drawings.

BRIEF DESCRIPTION OF THE DRAWINGS

FIG. 1 is a partial longitudinal cross-sectional view of the distal end of a catheter containing an embolic device comprised of a sequence of miniature beads according to the present invention;

FIG. 2 is a longitudinal cross-sectional view of the embolic device of the present invention partially deployed from the distal end of a catheter into an aneurysm;

FIG. 3A is a side view of an embodiment of the embolic device of the present invention having a hook-type anchor element disposed at one end;

FIG. 3B is a side view of an alternative embodiment of the embolic device of FIG. 3A having an anchor element formed of ingrowth material comprising thrombogenic fuzz;

DETAILED DESCRIPTION OF THE PREFERRED EMBODIMENT

Figure 4:
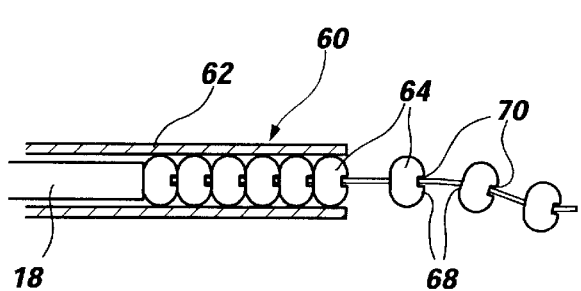
FIGS. 4–8 are side and partial longitudinal cross-sectional views of alternative embodiments of the embolic device of the present invention comprising beads with shapes other than spherical.

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

FIG. 1 shows the embolic device 10 of the present invention partially disposed within a catheter 12. As used herein, the terms embolic device, and thrombogenic device are used interchangeably to refer to the invention as a whole. However it will be apparent that the present invention may function in various ways. The device may be used to initiate thrombogenesis (the formation of a blood clot), angiogenesis (development of blood vessels), fibrogenesis (formation of fibrous tissue), or to form an embolism (an obstruction) in a body passageway. Additionally, the device may simply serve as a drug delivery device for delivering medicament to a selected target location within the anatomy.

The device 10 generally comprises a sequence of miniature beads 14 disposed along a flexible linear filament 16. It will be apparent that a flexible linear device, such as a string of beads, cannot normally resist compressive forces. However, when constrained within a tubular element, such as a catheter, a linear sequence of solid elements connected by a flexible filament can be pushed in a manner similar to a solid rod. When pushed, the solid elements (the beads) are forced together in a line as constrained by the catheter lumen, and the flexible filament typically assumes a slack configuration between solid elements.

The string of beads 10 must have adequate compression strength when constrained within the catheter 12 so that it may be pushed through the catheter with a plunger rod or wire 18, and out the distal end 12a of the catheter to the target location. Alternatively, the string of beads may be forced out of the catheter by injection of a liquid. A flexible string of beads is well suited to pushing through a catheter because it handles sharp curves well, and is inherently atraumatic. The beads 14 may be formed to slide and/or pivot on the filament 16, or may be fixedly attached thereto, or some combination thereof. For example, some of the beads may be fixed to the filament, with others being slidable on the filament. The fixed beads may even be integrally formed of the material of the filament.

The beads 14 preferably have diameters of from 0.002 inches to 0.0018 inches, and may be made of a variety of biocompatible materials, including polymers, radiopaque polymers, metals, metal alloys, etc. By selecting the material of the beads, a user may control the density of the string. For example, suitable polymer materials such as polyethylene or polypropylene will form beads having a density less than blood. However, if the beads are made of metals, such as platinum or platinum alloy, the resulting device would have a density greater than blood. It will be apparent that individual beads could also be formed of more than one material, such as a polymer bead with a coating of platinum or other biocompatible metal. The string of beads may also be comprised of beads of several different materials, placed in such a fashion as to provide the desired density and/or to perform other functions.

The beads may be alternatively formed of magnetized material, and stick together within the body cavity to form the desired thrombogenic mass. Alternatively, the catheter or other delivery means, or even the beads themselves, could provide a chemical agent such as a hydrophobic adhesive which causes the beads to adhere to each other in the desired location.

The surface of the beads 14 may be chemically treated or coated to make them very thrombogenic. The surface is preferably roughened or made porous. Additionally, the beads may be irregularly shaped to present a larger exterior surface, and this, along with the porosity, serves to promote thrombogenicity. To prevent or reduce the formation of thrombus during implantation and manipulation of the device, the beads 14 are preferably provided with a coating of a blood soluble polymer, such as polyvinyl alcohol. This coating allows the device to be easily manipulated for a period of time without clotting, until the coating dissolves. During delivery of the device, the coating inhibits thrombosis. After a brief time, however, the coating dissolves, allowing thrombosis to begin. The beads and filaments themselves may also be configured to dissolve, so that when the device has performed its task there are no foreign objects remaining in the body which can be swept away to cause unwanted blockage or clotting.

At the time of delivery of the thrombogenic device, drugs of various kinds may be delivered to the target location through catheter 12. However, drugs typically desired for use in combination with thrombogenic devices are generally desired to be present and released slowly over a long period of time. Moreover, these drugs are frequently not wanted on the surface, but inside the tissue. Accordingly, the beads 14 may be either porous or hollow, and may be impregnated (if porous) or filled (if hollow) with a medicament for controlled release into the interior of the body. With porous beads, the medicament solution would be absorbed into the bead by the capillary effect, and then when the bead is deposited at the target site, the solution will be discharged by diffusion—by blood flowing therepast and thereabout. The beads themselves may also be soluble, whether hollow or merely porous, allowing the drug contained therein to be slowly released as the bead dissolves. Examples of medicaments which may be delivered by this method include clotting factors (to encourage thrombosis), vascular endothelial growth factors (to promote revascularization), or anti-angiogenesis drugs for control of tumor growth. It will be apparent that other drugs may be delivered in this way.

The filament 16 can be multi or mono filament polymer or single or multistrand metal, and can be malleable or resilient. Accordingly, the mechanical properties of the filament may be carefully controlled to achieve the desired operation. For example, resilient filaments may be formed to have a preferred memory position, such as straight, or curved, or may have a predetermined shape, such as a ball or helical coil, or tangled "fuzz." With spring-like properties, as the string of beads is packed into a body cavity, the spring force helps bias the device within the cavity, particularly where the cavity has a small neck. Alternatively, the filament may be formed of malleable material, such as copper or other metal, so that when the filament is bent, twisted, and packed into place it retains its contorted shape.

The string of beads as described is less likely to break or cause tissue damage than other embolic devices because it is flexible and does not have sharp edges. For example, it is well known that implantable rigid devices, including drug delivery devices such as Norplant®, tend to be moved by the flexing of muscles, and occasionally cut through body tissues, such as emerging through the skin. The flexible string of beads is also less likely to migrate within the body because when one end becomes dislodged, its movement is less likely to cause the other end to also become dislodged because of the flexibility of the filament.

Referring to FIG. 2, there is shown a side, cross-sectional view of a blood vessel 24 in which an aneurysm 26 is shown formed in one side of the vessel. A fragmented view of a catheter 12 is shown threaded in the vessel 24, with a distal end 12a positioned adjacent the neck 28 of the aneurysm 26. In use, the catheter 12 is threaded through the vasculature or body passageway 24 to the site at which the embolic device 10 is to be disposed. The purpose of such disposal, for example, is to provide an occlusion in the passageway to allow for coagulation of blood to prevent further flow, or to cause scarring in the aneurysm 26 to thereby fill the aneurysm with scar tissue to prevent the bursting thereof, etc.

In FIGS. 1 and 2 the string of beads 10 is shown as being coiled or tangled within the aneurysm 26, but when threaded through the catheter 12 it is straightened to allow it to be pushed. Then when the end section is pushed out the terminal end 12a of the catheter, it resumes a coiled or tangled condition as shown, to substantially fill and pack the aneurysm with a tangled mass of the interconnected miniature beads. As noted, if the filament is formed of a malleable material, the string of beads may be twisted and packed into the cavity to form a tangled mass which retains the tangled shape. If it is formed of a material having spring properties, it will tend to push against the sides of the aneurism, and thus hold itself within the cavity.

It will be apparent that the string of beads may be preconfigured to a desired length before insertion into the delivery catheter. Then the entire string of beads may be delivered to the target location, and the pushing device and delivery catheter may then be removed. Alternatively the string of beads may have a length which is longer than actually needed. In such cases, when a suitable quantity of the string of beads is extended beyond the distal end of the catheter to the target location, the distal end of the string of beads may be severed or cut from the remainder of the string, and the unused string may be withdrawn with the pushing device and the catheter. Severance of the distal end of the string of beads may be accomplished by a number of methods.

Figure 12:
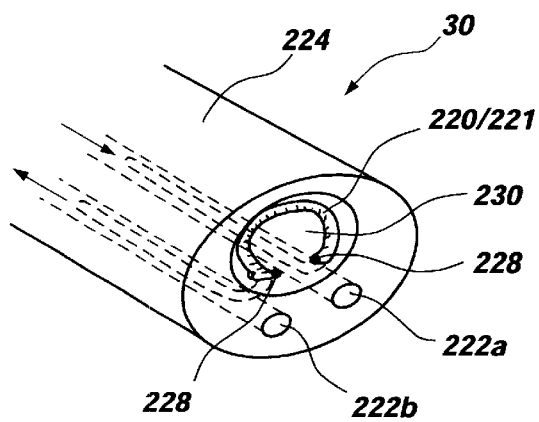
FIG. 12 is a partial sectional-pictorial view of a three-lumen catheter incorporating a cutting device for cutting the string of beads according to the present invention.

The delivery catheter 12 may be configured with a cutting device 30 at its distal end 12a for cutting the embolic device 10 at the end of a given procedure. One embodiment of a suitable cutting device 30 is shown in more detail in FIGS. 12 and 13. The cutting device 30 comprises a high strength flexible cutting filament 220, such as a Kevlar® fiber, which is threaded through two minor lumens 222a and 222b formed generally in one side of a three-lumen catheter 224. Near the distal end 226 of the catheter 224, the two minor lumens are provided with openings 228 which communicate with the major lumen 230 of the catheter. The major lumen 230 is the passageway through which the string of beads is extended. The cutting filament 220 extends from the proximal end of the catheter through the first minor lumen 222a, through the corresponding opening 228, into the major lumen 230 of the catheter where it forms a loop 221 around the periphery of the major lumen, and extends into the opening 228 associated with the second minor lumen 222b and back toward the proximal end of the catheter. At least the loop portion 221 of the cutting filament 220 preferably has an abrasive surface, so as to allow cutting of the linear filament 16 of the string of beads via a sawing motion if needed. The cutting filament 220 may also be non-abrasive, and cut the linear filament simply by breaking it.

Figure 13:
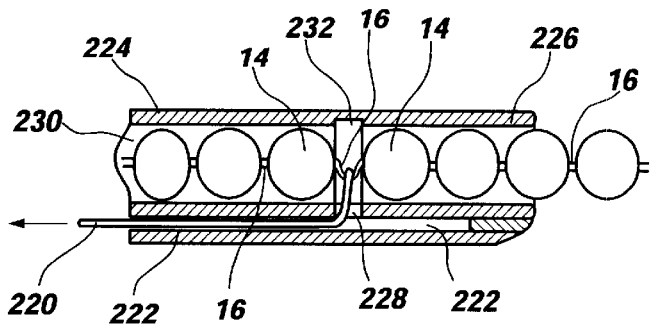
FIG. 13 is a longitudinal cross-sectional view of the catheter of FIG. 12 showing the cutting device in use.

Within the major lumen 230 of the catheter, the cutting filament 220 resides within a recess or niche 232, shown more clearly in FIG. 13, formed in the side wall of the catheter in the region of the openings 228. This niche allows the loop 221 of the cutting filament 220 to be out of the way and not obstruct the major lumen of the catheter during extension and placement of the string of beads. When a desired number of beads 14 have been extended beyond the distal end of the catheter, the user then pulls on the proximal end of the cutting filament, which extends out the proximal end of the triple lumen catheter, drawing the filament loop 221 out of the recess 232, toward the openings 228, and transversely onto the linear filament 16. Depending upon the material of the linear filament 16, the user may cut the string of beads simply by breaking the linear filament 16 by pulling on one end of the cutting filament 220. Alternatively, the user may cut the string of beads by performing a sawing motion—alternately pulling on first one end, then the other end, of the cutting filament 220. If the linear filament 16 is formed of a relatively weak polymer material, it may be cut or broken simply by pulling on the proximal end of the cutting filament. However, if the linear filament 16 is formed of a stronger material, such as metal, it may require a sawing action to sever.

Viewing FIG. 13, it will be apparent that as the cutting filament 220 draws transversely upon the linear filament 16, it will tend to draw the two nearest adjacent beads 14 together. This can be advantageous. Those skilled in the art will recognize that when the two adjacent beads contact each other due to a transverse force on the filament therebetween, this will increase the tension in the linear filament 16, and will thereby provide additional leverage which will add to the cutting power of the cutting filament 220. By using the cutting filament as described, the user may cut the linear filament 16 at the distal end of the catheter to detach the device 10 at the target location, allowing the catheter and other implements to be retracted from the target location and removed from the patient.

As an alternative to direct mechanical cutting or sawing of the linear filament 16 with a cutting filament, the linear filament may be severed by means of mechanical vibration. The linear filament may be connected to a pusher rod 18, which is provided with a discontinuity 32 toward its distal end (see FIG. 1), which allows it to be detached by means of mechanical energy transmitted down the guidewire. For example, after the string of beads 10 has been guided to the desired target site, an ultrasound generator (not shown) would be connected to the proximal end of wire 18 and an ultrasound signal applied thereto. The frequency and amplitude of the signal (observed on a spectrum analyzer) would be selected to produce high stress in the discontinuity 32, depending on the natural frequency of the pusher rod 18 and attached string of beads 10, fatiguing the wire 18 so that it breaks, ruptures, or otherwise separates at the discontinuity, leaving the string of beads at the target location. Because the system uses vibrations in the ultrasonic range, the separation is accomplished rapidly, reliably and without pain to the subject.

Alternatively, discontinuities may be provided at selected locations on the linear filament itself, such as between fixedly attached beads, to allow severance of the string of beads at a desired location through mechanical vibration as described above. A more detailed description of an endovascular wire device with a distal end detachable by means of mechanical vibrations is outlined in U.S. Pat. No. 6,022,369, the disclosure thereof being incorporated herein by reference.

As noted above, the string of beads 10 may be comprised of beads of several different materials, placed in such a fashion as to provide the desired density and/or to perform other functions. For example, as shown in FIG. 2, the string may be made with a repeating pattern of one heavy metal bead 34, followed by several lighter polymer beads 36. The number of polymer beads may be selected to precisely control the average density of the resulting string. Moreover, the metal bead may be formed of platinum, for example, to serve as a radiopaque marker to assist in insertion and precise placement of the device.

The body's own clotting is generally sufficient to anchor the device in place. Alternatively, an end of the string of beads could be fixed at a suture point, or within cauterized adjacent tissue. As another alternative, the linear sequence of beads could be provided with an anchor element on one end for anchoring the string of beads in body tissues, and thereby prevent migration of the string of beads. One application of the present invention is in treatment of cardiac damage. A recently developed method of restoring blood flow to damaged regions of the cardiac muscle involves puncturing the heart muscle (usually only partway through) using a laser, typically from within a chamber of the heart, so as to form one or more small holes in the wall of the heart. These holes create a wound which triggers angiogenesis, spurring the formation of collateral blood vessels and capillaries which restore blood flow around damaged or blocked arteries to regions of the heart muscle suffering from inadequate blood flow.

In this procedure, clotting may be spurred by the introduction of the string of beads into the hole or holes. In this application, the string of beads is provided with an anchor element at one end, and the string is inserted into the hole or holes with the anchor element going first, the anchor element being configured to prevent the string from coming out of the hole. FIG. 3A is a side view of one embodiment of an embolic device according to the present invention having a hook-type anchor element 42 disposed at one end. The hook-type anchor element 42 comprises one or more protruding elements 44, which are tapered in a direction opposite the direction in which the device is to be pushed into the hole. The anchor 42 and the protruding elements 44 may be formed to be relatively rigid like the barbs on a fish hook, or may be relatively flexible like the bristles of a brush. Accordingly, the anchor 42 may be formed of relatively flexible material, such as biocompatible polymers, or more rigid material such as metal. Because the protruding elements are tapered opposite to the direction in which the anchor is inserted into the hole, when the anchor is forced into the hole, the protruding elements may deflect toward the center shaft of the hook, in the case of flexible protruding elements, or deflect the surrounding tissue, in the case of more rigid protruding elements, allowing the anchor to slide into the hole relatively easily. Once in place, however, the protruding elements hook into the surrounding tissue to resist any force which tends to pull the string out of the hole.

Alternatively, the anchor element may comprise ingrowth material, which allows body tissue to grow around it, and thus becomes intertwined with the patient's natural tissue. FIG. 3B is a side view of the embolic device of FIG. 3A having an anchor element 50 comprised of a ball of thrombogenic fuzz. The fuzz is formed of a biocompatible material which allows body tissues to grow within the ball of fuzz, thus firmly anchoring the string of beads over a period of time. The ball of fuzz and the attached string of beads may be formed of a material which gradually dissolves in body fluids, thus allowing the device to serve its purpose of spurring new blood vessel growth, without creating a permanent foreign structure within the patient.

It will be apparent that the embodiments of FIG. 3A and FIG. 3B may be combined, such that the anchor comprises a hooked or barbed element with a ball of fuzz attached. This embodiment would provide the advantages of immediate mechanical anchorage provided by the hooks or barbs, with the gradually increasing anchor strength provided as the body tissues grow around the fuzz material.

Figure 3C:
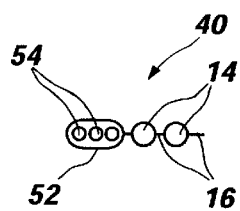
FIG. 3C is a side view of an alternative embodiment of the embolic device of FIG. 3A having a perforated plate anchor element.

As mentioned above, the anchor element could also be fastened within a suture point or in cauterized tissue. FIG. 3C is a side view of an embodiment of the embolic device of FIG. 3A having a perforated plate anchor element 52, which is configured to be attached at a suture point or within cauterized tissue. The openings 54 in the perforated plate 52 allow suture filaments to pass through the plate to hold it firmly in place. Alternatively, the openings 54 may help to hold the device in cauterized tissue, or mays assist in anchorage of the device of this and other embodiments described herein via biocompatible adhesives which are well known in the art. The adhesives may be activated by body heat or by contact with blood, and may also be configured to gradually dissolve in body fluids after the string of beads is anchored by surrounding tissue growth.

Figure 3D:
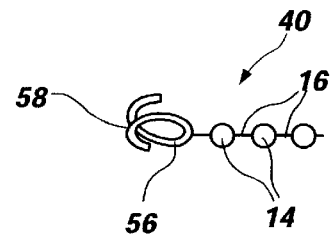
FIG. 3D is a side view of yet another alternative embodiment of the embolic device of FIG. 3A having a clip type anchor element.

FIG. 3D is a side view of yet another alternative embodiment of the embolic device of FIG. 3A having a clip type anchor element 56. The clip 56 may be formed of metals or polymers, and may take a variety of forms and operate on several different principles. As shown in FIG. 3D, the clip 56 comprises a loop of malleable metal, which is open at its distal end 58. When the string of beads is put in place, the distal end is positioned such that a quantity of body tissue is disposed within the opening, and the clip is then crushed or mashed so as to tightly grip the tissue. The malleable metal material deforms to the crushed configuration, causing the clip to retain its new compacted shape and hold the string of beads in place. Alternatively the clip may be formed of resilient material, whether metal or polymer, which is formed in a naturally closed position. When the string of beads is positioned at the target location, the clip may be forced open and attached to adjacent tissue. Because the resilient material of the clip tends to hold itself closed, the clip will firmly grip the tissue to anchor the string of beads in place. In the above embodiments wherein the device is used to insert into a hole, the string of beads device speeds the healing of the hole, and may also provide a means for the introduction of various drugs to speed the healing and angiogenesis process as described above.

The beads 14 may be formed in various shapes, other than spherical, to improve the pushability of the device in the catheter 12, and for other purposes. Various alternative shapes are shown in FIGS. 4–8. For example, as shown in FIG. 4, adjacent beads 64 of a string of beads 60 may be provided with flattened surfaces 68 on facing sides to allow them to "stack" against each other when pushed within the catheter 62. The flattened sides 68 may also be provided with a hollow or indentation 70 for receiving the slack filament 66 when the beads are pushed together.

Figure 5:
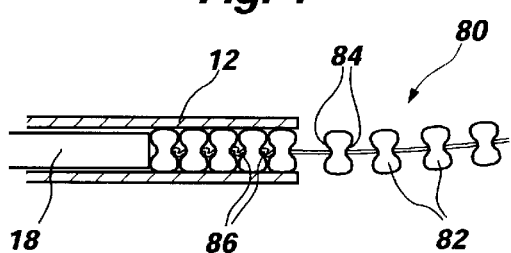

FIG. 5 depicts an alternative embodiment of a string of beads 80 wherein the beads 82 are generally round, and have indentations or hollows 84 formed on each side, such that the slack filament 86 may occupy the space of adjacent indentations 84 when the string of beads is pushed together.

Figure 6:
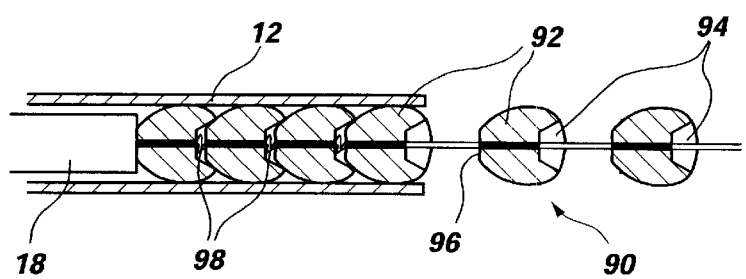
Figure 7:
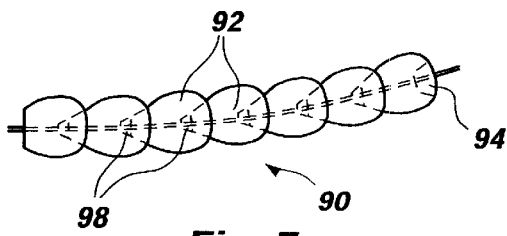

Alternatively, as shown in the sectional view of FIG. 6, the string of beads 90 may be comprised of a sequence of nesting beads 92. Each generally rounded bead 92 has an indentation 94 on a distal end, which is configured to conform to the shape of the proximal end 96 of the adjacent bead 92. This allows each bead 92 to receive the proximal end 96 of the preceding bead within its indentation 94, and to nest with its proximal end within the indentation of the following bead. The indentation 94 of each bead is also configured to accommodate the slack filament 98 when beads are pushed together. FIG. 7 provides a pictorial view of the embodiment of FIG. 6. From this view it is more apparent how the indentation 94 on the distal end of each bead 92 is configured to receive and partially surround the proximal end 96 of an adjacent bead when the beads are pushed together.

Figure 8:
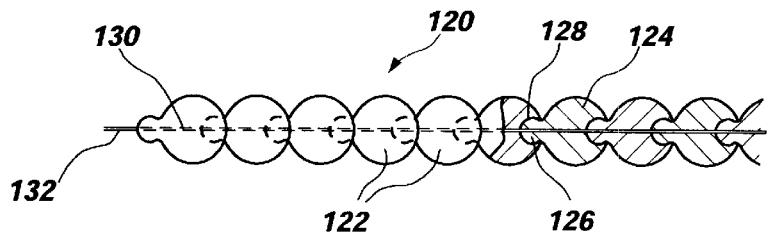

FIG. 8 shows an alternative embodiment of an embolic device 120 comprising a linear sequence of interlocking beads 122. Each bead 122 is comprised of a generally spherical main body portion 124, and a projecting lobe or ball 126. The main body portion comprises a socket 128 at its distal end, which is configured to receive the ball 126 of the preceding bead 122. By virtue of the ball and socket configuration, adjacent beads are free to pivot and/or rotate relative to each other, forming an elongate, flexible string of interconnected beads. The beads 122 preferably have main body diameters of from 0.004 to 0.018 inches.

The beads 122 also preferably have central bores 130 through which filament 132 is threaded to maintain the beads connected together in a chain. In the preferred embodiment, the beads are slidably disposed on the filament, and the string is allowed to tangle upon deployment from the catheter. Alternatively, deployment of the interlocking beads 122 may be carried out by inserting the string of beads, threaded on the filament 132, into a catheter. When the catheter is threaded through a vasculature passageway to the target site, the beads 122 may be deposited out the distal end of the catheter by retracting the filament 132 so that the particles fall off the end of the filament. When off the wire, each bead becomes disconnected from the adjacent rear particle when the ball 126 slides out of the socket 128. Alternatively, the ball and socket structure may be constructed to entirely hold adjacent beads together, so that an internal filament is not required to maintain the beads in the form of a flexible string.

It will be apparent that a variety of shapes and sizes of beads could be employed in the embodiment of FIG. 8, and a variety of interlocking or interconnecting mechanisms could be provided, in addition to the one shown. The beads might illustratively be made of platinum alloy or radiopaque polymer. Additionally, the central filament 130 could be preformed to assume a "fuzzball" or other desired shape when released from the distal end of the catheter. The beads would serve to reduce the chance of the fine central filament causing trauma to the vessel wall by increasing its effective diameter while not increasing its bending stiffness substantially.

Figure 9:
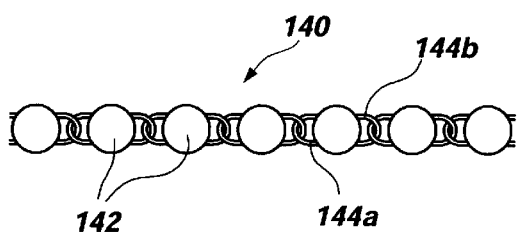
FIG. 9 is a pictorial view of an alternative embodiment of the embolic device of the present invention comprising a chain of linked beads.

As with a string of beads, a chain likewise cannot normally resist compressive forces. However, when constrained within a tubular element, such as a catheter, an ordinary chain can be pushed in a manner similar to a solid rod. Accordingly, the present invention can be configured as a chain of linked elements, in addition to a string of beads. FIG. 9 shows an alternative embodiment of an embolic device 140 comprising a chain of linked beads 142. In this embodiment, each bead 142 comprises a pair of oppositely directed links 144a and b, which are interconnected with similar links of adjacent beads to form a chain, rather than being disposed upon a filament. The beads and links may be formed of polymers, metals, or any other suitable biocompatible material. As with the basic embodiment, the chain of linked beads 140 may be pushed through a catheter for disposition at a target location, where it may fold back upon itself in a tangled mass to promote thrombosis.

Figure 10:
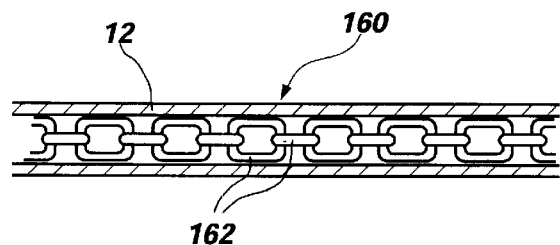
FIG. 10 is a partial longitudinal cross-sectional view of an alternative embodiment of the embolic device of the present invention comprising a chain of links.

In a similar embodiment, rather than linked beads, the device may simply comprise a chain 160 as shown in FIG. 10. This embolic device 160 comprises a plurality of links 162 which are formed in the manner of ordinary chains. As with the linked beads, the embolic chain may also be formed of polymers, metals, or any other suitable biocompatible material. The flexible nature of the chain allows it to tangle or curl up when released to occupy the desired volume, and the plurality of hollow spaces within the chain links helps encourage clotting by providing many small spaces for trapping blood and fluid.

Figure 11:
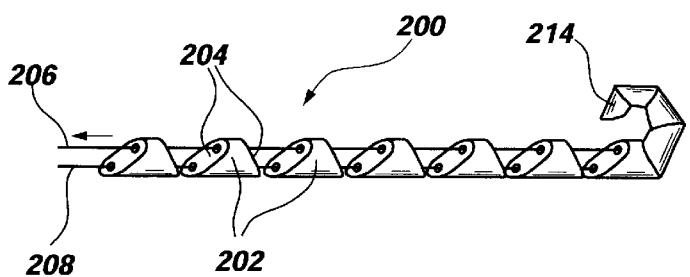
FIG. 11 is a pictorial view of an alternative embodiment of the embolic device of the present invention comprising a sequence of beads having faceted ends and a pair of filaments disposed therein.

FIG. 11 shows an alternative embodiment of an embolic device 200 comprising a sequence of beads 202 having faceted ends 204 and a pair of filaments 206 and 208 disposed therethrough. In this embodiment, the beads 202 have two parallel lumens 210 and 212 through which filaments 206 and 208 slidably pass, and are fixedly anchored in an end bead 214. When tension is applied to one of the filaments, the facets 204 of opposing beads are pulled together, causing the sequence of beads 202 to contract into a curved shape. The curved shape may take many forms, depending on the geometry of the beads. For example, the facets may be configured so that when contracted the string of beads forms a circular shape, a helical shape, or some other desired shape. Alternatively, the facets may be randomly configured, causing the string of beads to form a randomly curved and twisted shape when the filaments are pulled. Forming the string of beads into a curved or twisted shape advantageously reduces the chance that the device will escape from the target location.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A device configured for threading through a body passageway to a target location, comprising:
   a flexible elongate filament;
   a linear sequence of miniature beads permanently disposed upon the elongate filament; and
   wherein the device is configured to be threaded through a catheter to a target location and extended beyond a distal end of the catheter so as to occupy a volume of space at the target location.

2. The device of claim 1, wherein the beads are generally spherical in shape.

3. The device of claim 2, wherein the beads further comprise hollow indentations formed on opposing sides of adjacent beads to accommodate a slack portion of filament disposed therebetween when adjacent beads are pushed close together.

4. The device of claim 2, wherein the beads are formed of materials selected from the group consisting of polymers, radiopaque polymers, metals, and metal alloys.

5. The device of claim 4, wherein the surface of the beads is roughened by a processes selected from the group consisting of chemical treatment and the application of a coating.

6. The device of claim 5, further comprising a blood soluble lubricious coating disposed over the beads to facilitate threading the device through the catheter to the target location.

7. The device of claim 1, further comprising at least one medicament contained within the beads, whereby the at least one medicament may be delivered to the target location.

8. The device of claim 7, wherein at least some of the beads are porous, and the medicament is impregnated within the pores.

9. The device of claim 7 wherein at least some of the beads define a hollow therein, and the medicament is contained within the hollow.

10. The device of claim 7, wherein the medicament is selected from the group consisting of thrombogenic drugs, vascular endothelial growth factors, adhesive compounds for causing adjacent beads to adhere to each other, and anti-angiogenesis drugs.

11. The device of claim 1, wherein a distal end of the device is detachable.

12. The device of claim 11, further comprising severing means for severing the elongate filament.

13. The device of claim 12, wherein the severing means comprises a cutting filament disposed within the distal end of the catheter and positioned for cutting the elongate filament in response to tension applied to a proximal end of the cutting filament.

14. The device of claim 13, wherein the cutting filament comprises an abrasive filament configured to cut the elongate filament by means of a sawing action.

15. The device of claim 12, wherein the severing means comprises:
   a major lumen disposed in the catheter and configured for accommodating the linear sequence of beads;
   first and second minor lumens disposed in the catheter and configured for accommodating a cutting filament;
   first and second openings connecting the major lumen to the first and second minor lumens near the distal end of the catheter;
   a cutting filament extending through the first minor lumen from a proximal end of the catheter, through the first opening, through the second opening, and through the second minor lumen to the proximal end of the catheter, the filament forming a loop between the first and second openings within the major lumen, and configured for cutting the elongate filament of the string of beads in response to tension applied to a proximal end of the cutting filament.

16. The device of claim 15, further comprising an annular recess formed on an inside wall of the major lumen, such that the cutting filament may be disposed within the annular recess to accommodate use of the major lumen for extending and positioning the linear sequence of beads.

17. The device of claim 12, wherein the severing means comprises a discontinuity associated with the linear sequence of beads, the discontinuity being configured to rupture when mechanical energy is applied to the device.

18. The device of claim 17, wherein the discontinuity is formed in the elongate filament.

19. The device of claim 17, wherein the discontinuity is formed in a pushing rod connected to the elongate filament.

20. The device of claim 1, further comprising an anchor element disposed at an end of the device.

21. The device of claim 20, wherein the anchor element is a device selected from the group consisting of a hook with at least one protruding element, a ball of ingrowth material, a hook and ingrowth material combined, a perforated plate, and a clip.

22. The device of claim 20, wherein the anchor element is configured to be anchored in place by means selected from the group consisting of anchorage in cauterized tissue, anchorage with biocompatible adhesive, and anchorage with sutures.

23. The device of claim 1, wherein the beads are soluble in bodily fluids.

24. The device of claim 23, wherein the filament is soluble in bodily fluids.

25. The device of claim 1, wherein the elongate filament and at least some of the linear sequence of beads are integrally formed of the same material.

26. The device of claim 1, wherein the beads are magnetic.

27. The device of claim 1, wherein the elongate filament is malleable.

28. The device of claim 1, wherein the elongate filament is formed of material having spring properties.

29. The device of claim 1, wherein the beads comprise flattened surfaces on facing sides to allow adjacent beads to stack against each other when pushed through the catheter.

30. The device of claim 1, wherein the beads comprise nesting indentations to enhance pushability of the string of beads through the catheter.

31. The device of claim 30, wherein the nesting indentations comprise an indentation in a distal end of each bead, and a curved surface formed on the proximal end of each bead, whereby said indentation mates with the curved surface of an adjacent bead when pushed there against.

32. The device of claim 1, wherein the beads further comprise a hollow indentation formed on the distal sides of each bead to accommodate a slack portion of filament disposed therebetween when adjacent beads are pushed close together.

33. The device of claim 1, wherein the beads further comprise:
   a generally spherical body having a socket formed in a first end;
   a ball extending from a second end of the generally spherical body, configured to be received within the socket of an adjacent bead, whereby the string of beads may be pivotally interconnected by the balls and sockets of adjacent beads.

34. The device of claim 33, wherein the balls and sockets are releasably interconnected, such that the beads may separate when the filament is removed.

35. A method of initiating an event in a body passageway, comprising the steps of:
   inserting a catheter into the body passageway, and threading the catheter until a distal end of the catheter reaches a target location;
   inserting a linear string of miniature beads permanently disposed upon a filament into a proximal end of the catheter;
   pushing the string of beads through the catheter toward the distal end thereof with a pushing device;
   pushing the string of beads out of a distal opening of the catheter at the target location; and
   removing the catheter and pushing device from the body passageway.

36. The method of claim 35, further comprising the step of causing the string of beads to assume a generally tangled mass at the target location.

37. The method of claim 36, further comprising the step of injecting a medicament into the mass, the medicament being selected from the group consisting of vascular endothelial growth factor, adhesive compounds for causing adjacent beads to adhere to each other, and anti-angiogenesis drugs.

38. The method of claim 35, further comprising the step of anchoring the string of beads within the body passageway at the target location.

39. The method of claim 35, wherein the event is selected from the group consisting of a thrombogenic event, a fibrogenic event, and an angiogenic event.

* * * * *